(12) United States Patent
Bazilev et al.

(10) Patent No.: US 9,168,128 B2
(45) Date of Patent: Oct. 27, 2015

(54) VALVED AORTIC ROOT PROSTHESIS

(71) Applicant: ZAO NPP MedEng, Penza (RU)

(72) Inventors: Vladlen V. Bazilev, Penza (RU); Sergei V. Evdokimov, Penzenskaya obl. (RU); Aleksandr S. Evdokimov, Penzenskaya obl. (RU); Evgenii V. Rosseikin, Penza (RU)

(73) Assignee: ZAO NPP MedEng, Penza (RU)

( * ) Notice: Subject to any disclaimer, the term of this patent is extended or adjusted under 35 U.S.C. 154(b) by 0 days.

(21) Appl. No.: 14/198,553

(22) Filed: Mar. 5, 2014

(65) Prior Publication Data
US 2014/0188214 A1 Jul. 3, 2014

Related U.S. Application Data

(63) Continuation of application No. PCT/RU2012/000730, filed on Sep. 5, 2012.

(30) Foreign Application Priority Data

Sep. 6, 2011 (RU) .................................. 2011136908

(51) Int. Cl.
*A61F 2/24* (2006.01)
*A61F 2/06* (2013.01)

(52) U.S. Cl.
CPC .................. *A61F 2/24* (2013.01); *A61F 2/2409* (2013.01); *A61F 2/2412* (2013.01); *A61F 2/06* (2013.01); *A61F 2002/061* (2013.01); *A61F 2220/0075* (2013.01); *A61F 2250/0069* (2013.01); *A61F 2250/0097* (2013.01)

(58) Field of Classification Search
CPC .... A61F 2/06; A61F 2/2412; A61F 2002/061
USPC ............................ 623/2.12–2.19, 2.36–2.238
See application file for complete search history.

(56) References Cited

U.S. PATENT DOCUMENTS

| | | | |
|---|---|---|---|
| 7,320,704 B2 * | 1/2008 | Lashinski et al. | 623/2.11 |
| 7,534,259 B2 * | 5/2009 | Lashinski et al. | 623/2.1 |
| 7,575,592 B2 * | 8/2009 | Woo | 623/1.26 |
| 8,267,993 B2 * | 9/2012 | Nguyen et al. | 623/2.11 |
| 8,734,506 B2 * | 5/2014 | Bulman-Fleming et al. | 623/2.36 |
| 2005/0065597 A1 * | 3/2005 | Lansac | 623/2.11 |
| 2008/0082161 A1 * | 4/2008 | Woo | 623/1.26 |
| 2013/0046379 A1 * | 2/2013 | Paolitto et al. | 623/2.19 |
| 2013/0073033 A1 * | 3/2013 | Bulman-Fleming et al. | 623/2.11 |
| 2014/0081391 A1 * | 3/2014 | Ruyra-Baliarda et al. | 623/2.17 |
| 2014/0088697 A1 * | 3/2014 | Fogarty et al. | 623/2.18 |
| 2014/0288642 A1 * | 9/2014 | Yoshida et al. | 623/2.17 |
| 2014/0330372 A1 * | 11/2014 | Weston et al. | 623/2.18 |
| 2014/0350666 A1 * | 11/2014 | Righini | 623/2.11 |

* cited by examiner

*Primary Examiner* — Suzette J Gherbi
(74) *Attorney, Agent, or Firm* — Arent Fox LLP; Michael Fainberg

(57) ABSTRACT

Disclosed herein a valved aortic root prosthesis comprising a vascular prosthesis with a cuff fastened to the proximal end thereof and a valve mounted in the cuff, wherein the cuff is provided with three marks at an angle of 120 degrees from each other, which divide the cuff into three zones corresponding to the right coronary sinus, the left coronary sinus and the non-coronary sinus, while the vascular prosthesis is provided with two apertures situated above the zones corresponding to the right and left coronary sinuses, wherein the aperture in the left coronary sinus zone is provided at a level of 5-25 mm from the cuff, and the aperture in the right coronary sinus zone is provided at a level of 25-55 mm from the cuff, and each aperture has a vascular prosthesis sewn thereto for connection to the adjacent coronary artery.

1 Claim, 3 Drawing Sheets

VALVED AORTIC ROOT PROSTHESIS

CROSS-REFERENCE TO RELATED APPLICATION

This application is a continuation of International Application No. PCT/RU2012/000730, filed Sep. 5, 2012, which claim benefit of priority to Russian Application No. 2011136908, filed Sep. 6, 2011.

TECHNICAL FIELD

The invention generally relates to medical technology and particularly to a valved aortic root prosthesis that can be used in cardiac surgery.

BACKGROUND

Aortic roots (AR) for use in cardiac surgery are known which are taken either from animals (xenograft—XG)) or from the corpse of a human being (homograft (HG). (See, e.g., Ross, D N, Homograft replacement of the aortic valve. Lancet 1962; 2: 447).

A frameless aortic valve bioprosthesis is known which is manufactured from a valve/aorta complex of a mammal, comprising a tubular body and a multi-valve sealing element abutting the end of the tubular body (see e.g., U.S. Pat. No. 4,443,895).

A frameless aortic root prosthesis is known (see e.g., U.S. Pat. No. 5,123,919) comprising a vascular prosthesis of synthetic tissue with a cuff fastened on the proximal end and a mechanical valve mounted in the cuff.

All the above prostheses, though successfully fulfilling their functional task, have an essential shortcoming. While the coronary arteries are sewn onto the prosthesis, the surgeon must do difficult manoeuvres in connection with the selection of the place for forming apertures in the wall of the vascular prosthesis, cauterising the apertures and sewing the coronary vessels onto them. Different complications can occur during this, due to, for instance, a distortion of the coronary artery, a seal failure of the connection of the artery with the vascular prosthesis and the like.

Therefore, there is a need for a valved aortic root prosthesis that simplifies the prosthesis implantation procedure and reduces risk of post-operative complications.

SUMMARY

Disclosed herein an improved valved aortic root prosthesis that comprises a vascular prosthesis with a cuff fastened to the proximal end thereof and a valve mounted in the cuff. The cuff is provided with three marks at an angle of 120 degrees from each other, which divide the cuff into three zones corresponding to the right coronary sinus, the left coronary sinus and the non-coronary sinus. The vascular prosthesis is provided with two apertures situated above the zones corresponding to the right and left coronary sinuses. The aperture in the left coronary sinus zone is provided at a level of 5-25 mm from the cuff, and the aperture in the right coronary sinus zone is provided at a level of 25-55 mm from the cuff, and each aperture has a vascular prosthesis sewn thereto for connection to the adjacent coronary artery.

The valved aortic root prosthesis provides a simplified procedure for implantation of the prosthesis and a reduced risk of post-operative complications.

The presence of the vascular prosthesis with the cuff fastened to the proximal end thereof and the valve mounted in the cuff in the valved aortic root prosthesis facilitate the functional working capacity of the prosthesis.

The provision of the three marks at an angle of 120 degrees from each other, which divide the cuff into three zones corresponding to the right coronary sinus, the left coronary sinus and the non-coronary sinus, makes the procedure of orientating the prosthesis during application of the sutures on the cuff and the fibrous ring of the valve undergoing replacement easier for the surgeon.

The provision of the two apertures in the vascular prosthesis situated above the zones corresponding to the right and left coronary sinuses makes it possible for the blood to pass from the vascular prosthesis into the coronary arteries.

The provision of the aperture in the left coronary sinus zone at a level of 5-25 mm from the cuff and of the aperture in the right coronary sinus zone at a level of 25-55 mm from the cuff facilitates an anatomical correspondence of the position of the apertures to the openings of the coronary vessels.

The sewing of additional vascular prostheses to each aperture of the vascular prosthesis for a connection to the adjacent coronary artery simplifies the procedure of applying the sutures that seal the zone linking the coronary arteries to the vascular prosthesis.

BRIEF DESCRIPTION OF THE DRAWINGS

The accompanying drawings illustrate one or more example aspects of the invention and serve to explain their principles and implementations.

DETAILED DESCRIPTION

Figure 1:
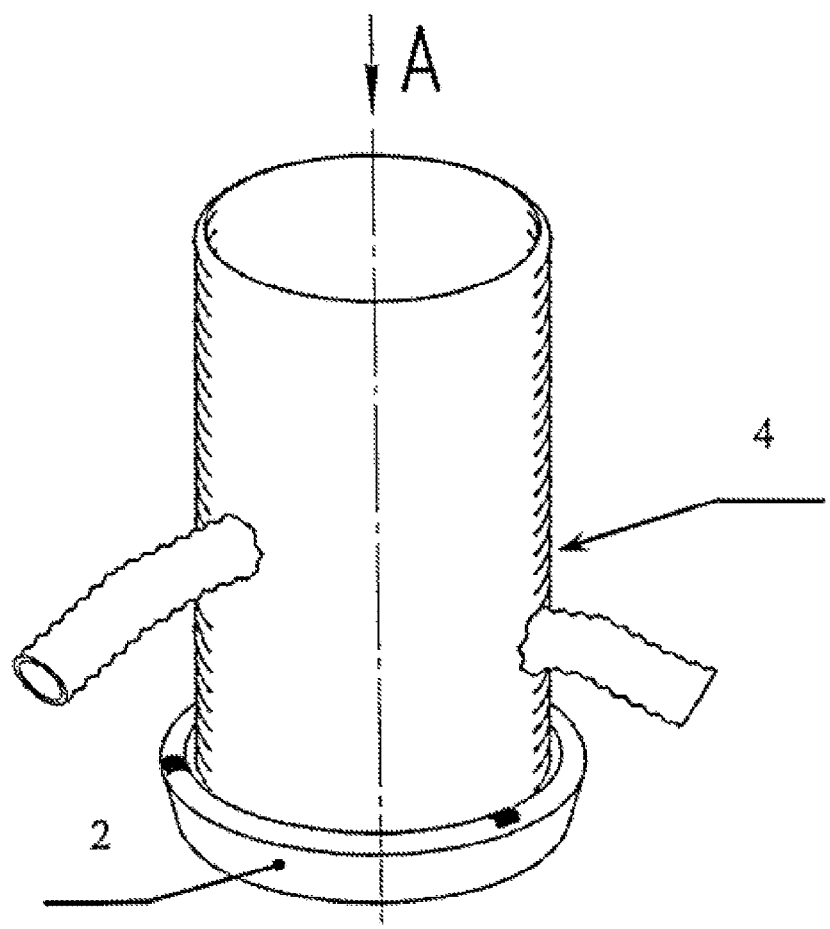
FIG. 1 shows the outer view of the valved aortic root prosthesis.
Figure 2:
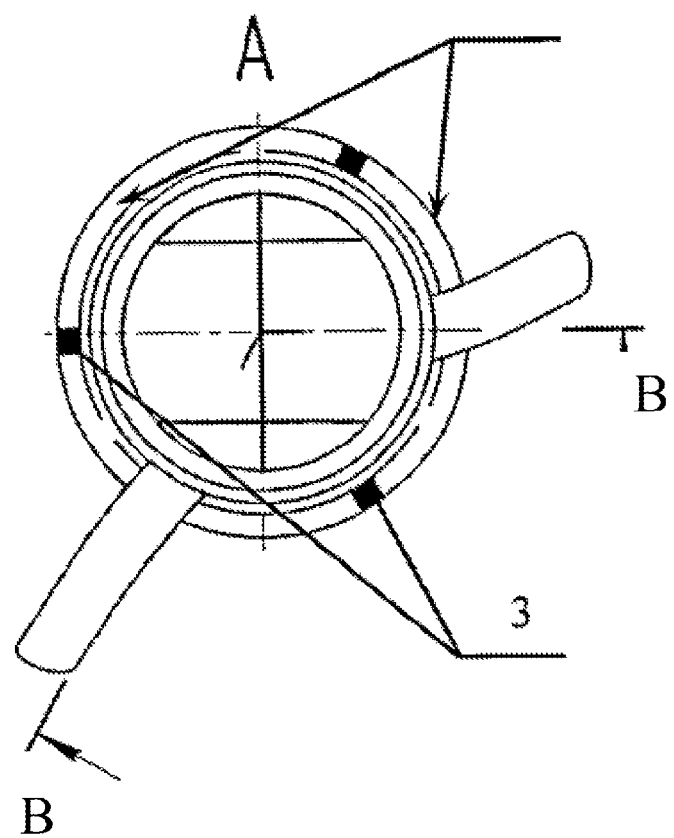
FIG. 2 shows a top view of the valved aortic root prosthesis.
Figure 3:
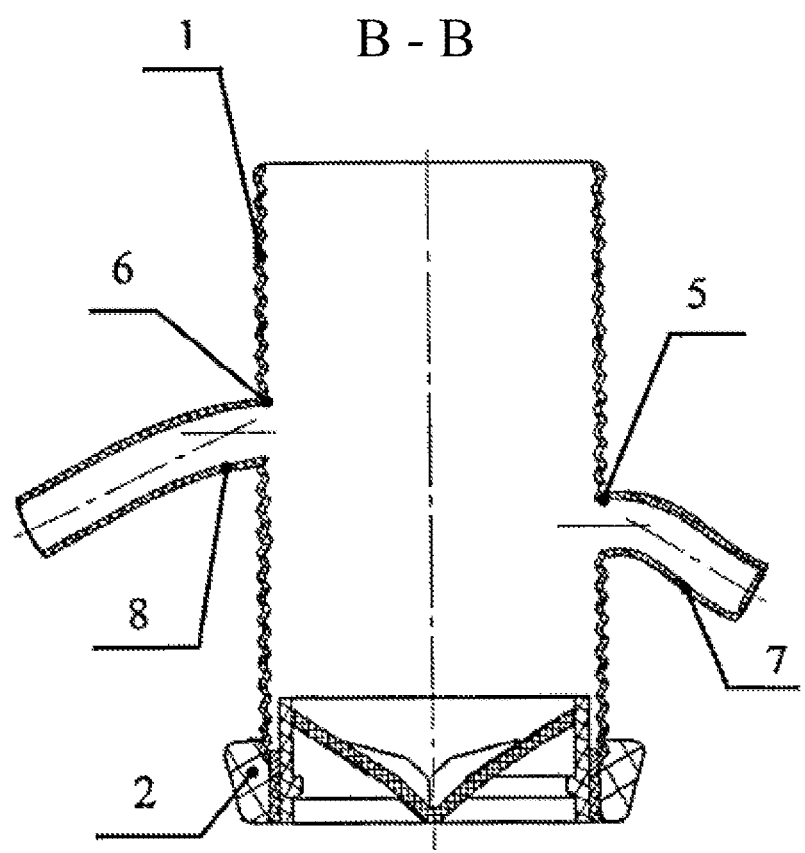
FIG. 3 shows the prosthesis in a longitudinal section.

As shown in FIGS. 1-3, a valved aortic root prosthesis comprises a vascular prosthesis 1 with a cuff 2 fastened to the proximal end thereof, and a valve mounted in the cuff 2. The cuff 2 is provided with three marks 3 at an angle of 120 degrees from each other, which divide the cuff into three zones 4 corresponding to the right coronary sinus, the left coronary sinus and the non-coronary sinus. The vascular prosthesis 1 is provided with two apertures 5 and 6 situated above the zones corresponding to the right and left coronary sinuses. The aperture 6 in the left coronary sinus zone is provided at a level of 5-25 mm from the cuff 2, and the aperture 5 in the right coronary sinus zone is provided at a level of 25-55 mm from the cuff 2. The exact level of the position of the apertures is defined by the anatomical characteristics of the patient, therefore it is recommended to have prostheses of differently dimensioned types with different levels of the aperture positions available during surgery. Each aperture 5 and 6 has a vascular prosthesis 7 and 8 sewn thereto for connection to the adjacent coronary artery.

The above-described valved aortic root prosthesis works as follows.

The damaged portion of the aorta with the valve is removed by means of standard surgical procedures used in aortic root replacements, isolating the ends of the coronary arteries. Further the surgeon, guided by the marks 3 on the cuff 2, orients the vascular prosthesis 1 in such a way that the sewn-on vascular prostheses 7 and 8 are situated in zones corresponding to the position of the right and left coronary sinuses. Subsequently the sutures are applied on the fibrous ring and the cuff 2. Upon completing the procedure of sewing the cuff 2 to the fibrous ring of the heart valve undergoing replacement, the surgeon successively cuts the vascular prostheses 7 and 8 to size until they contact the corresponding coronary artery, and sews the ends of the coronary arteries to the ends of the vascular prostheses 7 and 8. Since the vascular prostheses 7 and 8 have corrugated walls and are thus stretchable and flexible, this procedure is significantly easier than that of sewing the coronary vessels directly to the vascular prosthesis 1. Further the vascular prosthesis 1 is cut to size and sewn to the undamaged portion of the aorta.

The prosthesis 1 fills with blood. When a bleeding through the surgical sutures occurs, the surgeon has free access to the bleeding places and can eliminate them unhindered due to the stretchability and flexibility of the vessels 7 and 8.

While maintaining the all advantages of the most pertinent prior art, the proposed valved aortic root prosthesis provides a simplified procedure for implantation of the prosthesis and a reduced risk of post-operative complications.

In the interest of clarity, not all of the routine features of the aspects are disclosed herein. It will be appreciated that in the development of any actual implementation of the invention, numerous implementation-specific decisions must be made in order to achieve the developer's specific goals, and that these specific goals will vary for different implementations and different developers. It will be appreciated that such a development effort might be complex and time-consuming, but would nevertheless be a routine undertaking of engineering for those of ordinary skill in the art having the benefit of this disclosure.

Furthermore, it is to be understood that the phraseology or terminology used herein is for the purpose of description and not of restriction, such that the terminology or phraseology of the present specification is to be interpreted by the skilled in the art in light of the teachings and guidance presented herein, in combination with the knowledge of the skilled in the relevant art(s). Moreover, it is not intended for any term in the specification or claims to be ascribed an uncommon or special meaning unless explicitly set forth as such.

Those of ordinary skill in the art will realize that the above description is illustrative only and is not intended to be in any way limiting. Other aspects will readily suggest themselves to those skilled in the art having the benefit of this disclosure. Moreover, it would be apparent to those skilled in the art having the benefit of this disclosure that many more aspects and modifications than mentioned above are possible without departing from the inventive concepts disclosed herein.

The invention claimed is:

1. Valved aortic root prosthesis comprising:
a vascular prosthesis with a cuff fastened to the proximal end thereof and a valve mounted in the cuff,
wherein the cuff is provided with three marks at an angle of 120 degrees from each other, which divide the cuff into three zones corresponding to the right coronary sinus, the left coronary sinus and the non-coronary sinus, while the vascular prosthesis is provided with two apertures situated above the zones corresponding to the right and left coronary sinuses, wherein the aperture in the left coronary sinus zone is provided at a level of 5-25 mm from the cuff, and the aperture in the right coronary sinus zone is provided at a level of 25-55 mm from the cuff, and each aperture has a vascular prosthesis sewn thereto for connection to the adjacent coronary artery.

* * * * *